United States Patent [19]

Karsenty et al.

[11] Patent Number: 5,688,520
[45] Date of Patent: Nov. 18, 1997

[54] TRANSMUCOSAL DELIVERY OF MELATONIN FOR PREVENTION OF MIGRAINE

[75] Inventors: Herve Karsenty, Noisy le Roi; Luce Benes, Orleans; Francoise Horriere, Angerville; Claire La Coste, Paris, all of France

[73] Assignee: Minnesota Mining and Manufacturing Company, St. Paul, Minn.

[21] Appl. No.: 449,312

[22] Filed: May 24, 1995

Related U.S. Application Data

[63] Continuation-in-part of Ser. No. 412,717, Mar. 29, 1995, abandoned.

[51] Int. Cl.$^6$ .................................................. A61K 47/32
[52] U.S. Cl. ......................... 424/434; 424/435; 514/772.6
[58] Field of Search ................................ 424/434, 435; 514/772.6

[56] References Cited

U.S. PATENT DOCUMENTS

| | | | |
|---|---|---|---|
| 4,600,723 | 7/1986 | Short et al. | 514/416 |
| 4,615,697 | 10/1986 | Robinson | 604/890 |
| 4,654,361 | 3/1987 | Samples et al. | 514/419 |
| 4,945,103 | 7/1990 | Cohen | 514/419 |
| 5,113,860 | 5/1992 | McQuinn | 128/632 |
| 5,242,941 | 9/1993 | Lewy et al. | 514/416 |
| 5,385,736 | 1/1995 | Kappes et al. | 424/448 |
| 5,498,423 | 3/1996 | Zisapel | 424/464 |

FOREIGN PATENT DOCUMENTS

| | | |
|---|---|---|
| 2132512 | 3/1995 | Canada . |
| 0 438 856 A2 | 7/1991 | European Pat. Off. . |
| 0 518 468 A1 | 12/1992 | European Pat. Off. . |
| 91/06290 | 5/1991 | WIPO . |
| 93/23011 | 11/1993 | WIPO . |
| 95/03043 | 2/1995 | WIPO . |

OTHER PUBLICATIONS

*Ital. J. Neurol. Sci.*, 1986, 7, 319 (Toglia).
*Headache*, 1989, 29, 242 (Claustrat et al.).
SCRIP, "Migraine—Current Trends in Research and Treatment," May 1990, PJB Publications.
Mallo (Charles Mallo, Thesis, 26 Jan. 1988, L'universite Claude Bernard–Lyon I).
"Plasma Melatonin (M) and Sulfatoxymelatonin (aMT6s) Kinetics After Transmucosal Administration to Humans," 1993, Elsevier Science Publishers B.V. (Benes et al.).

*Primary Examiner*—Carlos A. Azpuru
*Attorney, Agent, or Firm*—Gary L. Griswold; Walter N. Kirn; Ted K. Ringsred

[57] ABSTRACT

A method of reducing the frequency of and/or preventing migraine, involving the step of administering melatonin, preferably to and across a mucosal surface, in an amount and for a time sufficient to increase the period of time between episodes of migraine.

7 Claims, No Drawings

TRANSMUCOSAL DELIVERY OF MELATONIN FOR PREVENTION OF MIGRAINE

This application is a continuation-in-part of application Ser. No. 08/412,717, filed Mar. 29, 1995, now abandoned.

BACKGROUND OF THE INVENTION

1. Technical Field

This invention relates to transmucosal drug delivery. In another aspect this invention relates to treatment or prevention of migraine. In yet another aspect this invention relates to therapeutic uses of melatonin.

2. Description of the Related Art

Transmucosal drug delivery systems are designed to deliver a therapeutically effective amount of drug across a mucosal surface, typically the oral mucosa, of a patient. Delivery of drugs across the oral mucosa avoids hepatic first-pass inactivation, poor or erratic absorption from the gastro-intestinal tract, inactivation by gastro-intestinal fluids, and other modes of inactivation characteristic of oral drug ingestion. Sustained release adhesive bandages, patches, and the like that contain drugs are known to the art.

Melatonin, N-[2-(5-methoxy-1H-indol-3-yl)ethyl]acetamide, is a hormone synthesized and secreted by the pineal gland. Melatonin shows a circadian variation with high nocturnal but low or undetectable diurnal plasma concentrations.

Melatonin has been studied in connection with a variety of indications. For example, U.S. Pat. No. 4,600,723 (Short et al.) and U.S. Pat. No. 5,242,941 (Lewy et al.) disclose the use of melatonin to treat circadian rhythm disorders (e.g., jet lag). U.S. Pat. No. 4,654,361 (Samples et al.) discloses the use of melatonin to lower intraocular pressure in a human having abnormally high intraocular pressure. U.S. Pat. No. 4,945,103 (Cohen) discloses the use of melatonin to treat premenstrual syndrome. European Patent Application 0 438 856 A2 (Fukuda et al.) discloses the use of melatonin to protect the skin against the influence of ultraviolet radiation. European Patent Application 0518468 A1 (Zisapel) discloses the use of melatonin to prevent sudden infant death syndrome.

Toglia (*Ital. J. Neurol. Sci.*, 1986, 7, 319) has asked whether migraine is due to a deficiency of pineal melatonin. Decreased plasma melatonin levels in migraine patients have been reported in *Headache*, 1989, 29, 241 (Claustrat et al.).

Migraine is a common condition. It is generally thought that at least 5–10% of the population suffer from some form of migraine, although estimates of the prevalence of migraine vary widely depending on the population studied and the criteria used to define migraine. It is generally accepted that women suffer migraine in greater numbers than men.

The cause of migraine headache is not well understood. Absent a clear aetiology, primarily descriptive approaches have been used in defining and classifying migraine. Symptoms can include headache, photophobia, nausea, vomiting, and a sensory disturbance known as an aura, which can involve visual disturbances (e.g., dimness of vision), numbness, and vertigo. The International Headache Society has proposed definitions and classifications that have come into common use. The two main classifications of migraine are common migraine (otherwise referred to as migraine without aura) and classical migraine (otherwise referred to as migraine with aura). Others classes include opthalmoplegic migraine, retinal migraine, and basilar migraine.

The acute symptoms of migraine can be treated with analgesics such as aspirin, paracetamol, ibuprofen, and the like, with ergotamine, and with antinauseants such as metoclopramide, domperidone, and phenothiazines. Many prophylactic treatments have been used, including clonidine, propranolol, calcium antagonists (verapamil, nifedipine), 5-hydroxytryptamine antagonists such as methysergide and pizotifen, and 5-hydroxytryptamine uptake inhibitors such as amitryptylene. There is much active research in the field (see, e.g., SCRIP, "Migraine—Current Trends in Research and Treatment", May 1990, PJB Publications. Mallo (Charles Mallo, Thesis, 26 Jan. 1988, L'universite Claude Bernard-Lyon I) describes intravenous infusion with melatonin in migraine patients.

SUMMARY OF THE INVENTION

It has been found that transmucosal delivery of melatonin is effective in increasing the period of time between episodes of migraine. Accordingly, this invention provides a method of reducing the frequency of and/or preventing migraine, comprising the step of administering melatonin in an amount and for a time sufficient to increase the period of time between episodes of migraine. This invention also provides for the use of melatonin in the manufacture of a pharmaceutical composition for use in reducing the frequency of and/or preventing migraine.

DETAILED DESCRIPTION OF THE INVENTION

The method of this invention involves delivery of melatonin. Melatonin is preferably delivered transmucosally, i.e., to and across a mucosal surface. Melatonin can be delivered to and across any mucosal surface of the body, e.g., the oral, nasal, vaginal, or rectal mucosa. Delivery to and across the oral mucosa such as the buccal mucosa, the gum, or the inner lip, is preferred. Drug administration is preferably begun on the day that a patient has an episode of migraine, about one to about five hours before the normal onset of sleep. Administration is continued throughout the normal period of sleep for a total cycle time of about 10–12 hours. The mount of melatonin delivered in each administration cycle is from about 0.05 to about 5.0 milligrams, and the administration cycle is repeated daily for at least the first two or three days after the onset of the migraine.

In the method of the invention melatonin can be delivered from any suitable device comprising a matrix containing melatonin and suitable for releasing it to a mucosal surface in the amount and over the time period set forth above. Melatonin can be present in the matrix in any suitable amount, which will vary with the particular matrix employed (e.g., on the basis of the propensity of the matrix to release the melatonin). Generally melatonin is present in an amount of about 0.1 to about 10 percent by weight based on the weight of the matrix.

The preferred matrix is a mucoadhesive matrix having melatonin dissolved or substantially uniformly dispersed in a mucoadhesive. A mucoadhesive for use in a device of the invention can be any composition that adheres to a mucosal surface and will release melatonin to the mucosal surface. Suitable mucoadhesives include those disclosed in U.S. Pat. Nos. 4,615,697 (Robinson) and 5,113,860 (McQuinn) (incorporated herein by reference).

Preferred mucoadhesive compositions include those disclosed in patent application Ser. No. WO 90/06505 incorporated herein by reference. Such preferred mucoadhesives comprise:

1) a particulate polymeric resin with an average particle size of less than or equal to about 100 μm, preferably between about 1 μm and about 80 μm, more preferably between about 1 μm and about 30 μm, and most preferably between about 2 μm and about 10 μm, and comprising at least about 55% by weight of carboxylic acid moieties based on the total weight of the polymeric resin; and 2) from about 20 parts to about 250 parts by weight of a hydrophobic elastomeric component, preferably about 20 parts to about 150 parts, and most preferably 25 to about 75 parts by weight, based on 100 parts by weight of the resin;

wherein the resin is dispersed substantially throughout the elastomeric component, and which composition contains less than about 10%, preferably less than about 6%, more preferably less than about 4%, and most preferably less than about 2% by weight of water based on the total weight of the resin.

A mucoadhesive matrix of this type preferably contains also about 0.1 to about 20 parts by weight, more preferably about 1 to about 10 parts by weight, of melatonin based on 100 parts by weight of the resin.

The polymeric resin component of the preferred mucoadhesive comprises at least about 55% by weight of carboxylic acid moieties based on the total weight of the resin. Suitable carboxylic acid-containing monomers include acrylic acid, maleic acid, itaconic acid, citraconic acid, methacrylic acid, and the like, and combinations thereof. Acrylic acid is preferred. The polymeric resin can also comprise minor mounts (e.g., less than about 20 percent by weight based on the total weight of all monomers in the polymer) of comonomers that are polymerizable with the carboxylic acid-containing monomer, such as methyl vinyl ether, lower alkyl (meth) acrylates, and the like.

Linear polyacrylic acid resins with a molecular weight between about 400,000 and about 5,000,000 have been found to be suitable for use in a composition of the invention. More preferred, however, are crosslinked resins. Most preferred resins include those comprising polyacrylic acid with a molecular weight between about 750,000 and about 4,000,000, preferably about 2,000,000 to about 4,000,000, and more preferably about 3,000,000, crosslinked with about 0.75% to about 2% by weight, based on the total weight of the resin, of a polyalkenyl polyether such as an allyl ether of sucrose or an allyl ether of pentaerythritol. Particularly preferred resins of this type include the resins available under the trade designation CARBOPOL™ resin (e.g., CARBOPOL™ resins EX165, EX214, 910, 934, 934P, 941, 951, 971, 974, and 1342 from B.F. Goodrich Co., Specialty Polymers and Chemical Division, Cleveland, Ohio). Another suitable resin is "polycarbophil", A.H. Robins Co., Richmond, Va., and described in U.S. Pat. No. XX as a polyacrylic acid crosslinked with divinylglycol.

The carboxylic acid moieties in the resin can be present as formal protonated carboxylic acid functional groups or as neutralized carboxylate salts. For example, a polyacrylic acid resin or a crosslinked resin such as those enumerated above can be partially neutralized by a base of an alkali metal, or by a base of a divalent or trivalent metal (e.g., $Zn^{+2}$, $Ca^{+2}$, $Mg^{+2}$, or $Al^{+3}$). Basic polyamines such as Eudragit E™ (a copolymer of dimethylaminoethyl methacrylate and neutral methacrylates, Rohm Pharma, Weiterstadt, Germany) are also suitable for use in neutralizing a resin. Preferred bases include NaOH.

Examples of materials suitable for use in an elastomeric component in these preferred mucoadhesives include: hydrocarbons such as block styrene-butadiene-styrene copolymers and block styrene-isoprene-styrene copolymers, such as those available from Shell Chemical Co. as Kraton™ rubbers, polyolefins such as polyisobutylenes such as VISTANEX™ LM-MH polyisobutylene (viscosity average molecular weight about 53,000), VISTANEX™ L-80 polyisobutylene (viscosity average molecular weight about 900,000), and VISTANEX™ L-100 polyisobutylene (viscosity average molecular weight about 1,200,000), all from Exxon Chemical, Houston Tex., polybutadienes, butyl rubber (a copolymer of isobutylene and isoprene), and isoprene rubbers, e.g., polyisoprene (such as that available as LIR-50 polyisoprene from Arakawa Chemical Co., Chicago, Ill. and NATSYN™ polyisoprene from Goodyear, Akron, Ohio); functionalized polyolefins such as functional polyisoprenes, e.g., carboxy-functional polyisoprenes (such as that available as LIR-410 polyisoprene, also from Arakawa) and hydroxy-functional polyisoprenes (such as that available as LIR-506 polyisoprene, Arakawa); and mixtures and blends of two or more of the foregoing. Hydrocarbons are the most preferred materials for use in an elastomeric component.

Gel, tablet, and powder matrices are also suitable. When the matrix is a gel it is preferably an aqueous gel comprising, in addition to the melatonin, a gel-forming agent. The gel-forming agent can be any pharmaceutically acceptable agent that is capable of forming a water based gel and does not have a detrimental effect on other components of the matrix. Examples of suitable gel-forming agents include gums (e.g., pectin); montmorillonite clays (e.g., Veegum); crosslinked polysaccharides (e.g., dextran crosslinked with epichlorohydrin) and polymeric acrylic resins (e.g., CARBOPOL™ resins, such as CARBOPOL™ 934P, CARBOPOL™ EX165, and CARBOPOL™ EX214, B.F. Goodrich, Specialty Polymers and Chemicals Division, Cleveland, Ohio, reacted with a base).

When the matrix is in the form of a tablet it preferably contains, in addition to the melatonin, a pharmaceutically acceptable binder. Examples of suitable binders include cellulose derivatives such as carboxymethylcellulose, hydroxypropylcellulose, or hydroxypropylcellulose; starches such as rice starch; silicas such as AEROSIL™ 200 colloidal silicon dioxide (Degussa Corp., Teeterboro, N.J.) and polymeric acrylic resins such as the CARBOPOL™ resins described above.

When the matrix is in the form of a powder it can be a lyophilized powder matrix, prepared by lyophilizing an aqueous gel that contains the melatonin. A powder matrix optionally contains additional components such as penetration enhancers (discussed below).

In some instances it may be necessary or desirable to incorporate a penetration enhancer into the matrix. Suitable penetration enhancers include anionic surfactants (e.g., sodium dodecyl sulfate); cationic surfactants (e.g., palmitoyl DL carnitine chloride); nonionic surfactants (e.g., laureth 9, polyoxyethylene 20 stearyl ether, polyoxyethylene 20 cetyl ether, polyoxyalkylenes); lipids (e.g., dodecanoyl L-a-phosphatidyl choline); bile salts (sodium deoxycholate, sodium taurodeoxycholate); and related compounds (e.g., sodium tauro-24,25-dihydrofusidate). The enhancers can be dissolved or dispersed substantially uniformly in the matrix.

The matrix can contain other ingredients, for example excipients such as flavorings or dyes and the like in amounts readily determined by those skilled in the art.

A device for use in the method of the invention preferably comprises a backing. The backing can be any flexible film that prevents bulk fluid flow, provides a barrier to loss of melatonin from the matrix, and is substantially inert to melatonin and other ingredients of the matrix. The backing material can be any of the conventional materials used as backings for tapes or dressings such as polyethylene, polypropylene, ethylene-vinyl acetate copolymer, polyurethane and the like. Also, a layer of hydrophobic elastomer can function as a backing. Preferred backing materials include an acrylate pressure sensitive adhesive coated polyurethane film such as TEGADERM™ surgical dressing (3M Company, St. Paul, Minn.).

A device involving a mucoadhesive matrix will remain in place on the mucosal surface owing to the mucoadhesive properties of the matrix.

In a device involving a matrix that is not itself a mucoadhesive, the melatonin-containing matrix is coupled with a mucoadhesive component (such as the mucoadhesive described above) in order that matrix it may be retained on the mucosal surface. Suitable configurations include a device wherein the matrix has a smaller periphery than the backing layer such that a portion of the backing layer extends outward from the periphery of the matrix. A mucoadhesive layer covers the outward extending portion of the backing layer such that the underside of the backing layer carries a layer of mucoadhesive around its periphery. The backing and the peripheral ring of mucoadhesive taken together form a reservoir which contains a melatonin-containing matrix (e.g., a tablet, gel, or powder). It may be desirable to incorporate a barrier element between the matrix and the mucoadhesive in order to isolate the mucoadhesive from the matrix. The barrier element is preferably substantially impermeable to water and to the mucosal fluids that will be present at the intended site of adhesion. A device having such a barrier element can be hydrated only through a surface that is in contact with the mucosa, and it is not hydrated via the reservoir.

A device of the invention can be prepared by general methods well known to those skilled in the art. The preferred mucoadhesives can be prepared according to the methods set forth in patent application Ser. No. WO 90/06505. Likewise a matrix can be readily prepared by those skilled in the art.

When the matrix is in the form of a gel, it is prepared by first combining water and the gel-forming agent to form a gel. Optional excipients such as penetration enhancers are added and mix to form a homogeneous gel. Melatonin is then added with mixing to homogeneity to afford a gel formulation. When the matrix is in the form of a tablet, a bulk powder formulation is initially prepared by combining the binding agent with optional excipients such as a penetration enhancer to form a homogenous mixture, then the melatonin is added and mixed to homogeneity. The bulk powder is then compressed using conventional means to form tablets. When the matrix is in the form of a powder, a bulk powder formulation as prepared for the tablets can be used or, alternatively, a gel formulation can be lyophilized to provide a powder.

Devices for use in the method of the invention and involving a mucoadhesive matrix can be prepared by the well known methods disclosed in patent application Ser. No. WO 90/06505 incorporated herein by reference. Reservoir type devices for use in the invention can be prepared by die cutting a sheet of mucoadhesive into individual patches such that a central portion of the patch is removed (e.g., a patch in the shape of a ring with an inner diameter of 1.3 cm and an outer diameter of 2.5 cm). A backing is then laminated to one surface of the mucoadhesive patch resulting in the formation of a reservoir. A matrix containing melatonin is then placed into the reservoir portion. Alternatively, a device involving a lyophilized powder matrix can be prepared by first preparing an aqueous gel matrix, filling it into the reservoir, and lyophilizing the resulting device.

The method of the invention was carried out in a double blind, comparative, randomized, placebo controlled multicenter study to determine safety and preventive efficacy of the patches in patients suffering from migraine. Devices used in the study were as follows:

Placebo

A solution containing a polyisobutylene with a viscosity average molecular weight of about 53,000 (60 g, as 92.3 g of a stock solution containing 65 percent by weight Vistanex LM-MH polyisobutylene in a 1:1 mixture by volume of hexane and toluene) and a polyisobutylene with a viscosity average molecular weight of about 1,200,000 (40 g, as 200 g of a stock solution containing 20 percent by weight of Vistanex L-100 polyisobutylene in a 1:1 mixture by volume of hexane and toluene) was prepared. This solution was then added to a suspension of Carbopol 934P (100 g) in 200 mL of a 1:1 mixture by volume of hexane and toluene. The resulting mixture was stirred for approximately two hours via a mechanical stirrer at 50–100 rpm. After this period, a vacuum was applied to the stirring mixture for approximately 10 minutes to remove bubbles before coating. The resulting mixture was then coated using a knife coater onto silicone-treated release liner at a wet thickness of approximately 3.4 mm. The solvent was allowed to evaporate at approximately 30° C. Individual patches were then handcut from this sheet material with a 0.5 cm$^2$ die. To the exposed surface of each individual patch was then added a backing material, TEGADERM™ 1625 brand surgical dressing, which had been previously cut into circular disks of 0.8 cm$^2$. This backing material was hand pressed to conform to the surface and the sides of each patch. The patch weight was approximately 50 mg (excluding the backing).

0.5 mg Melatonin

The method described above was employed, using 49.5 weight percent polyacrylic acid Carbopol 934P, 19.8 weight percent Vistanex L100 polyisobutylene, 29.7 weight percent Vistanex LM-MH polyisobutylene and 1 weight percent of melatonin. The melatonin was added as a powder to the stirring suspension of Carbopol 934P in hexane/toluene. Each patch contained approximately 0.5 mg melatonin; the patch weight was approximately 50 mg (excluding the backing).

1.0 mg Melatonin

The method described above was employed, using 49.0 weight percent polyacrylic acid Carbopol 934P, 19.6 weight percent Vistanex L100 polyisobutylene, 29.4 weight percent Vistanex LM-MH polyisobutylene and 2.0 weight percent melatonin. Each patch contained approximately 1.0 mg melatonin; the patch weight was approximately 50 mg (excluding the backing).

STUDY DESIGN

The patients selected for the study were men or women age 18–65 years who presented with acute migraine headache with or with out aura for more than one year at a rate of between 3 and 6 attacks per month in accordance with the criteria of the International Headache Society. Postmenopausal women were excluded.

For a run-in period of 4 weeks the patients were monitored. For the first migraine attack during this period each patient was treated with a placebo patch self-applied to the upper gum at 7 PM the day of migraine occurrence and removed at 7 AM on the following day. This administration cycle was repeated on the two days following migraine occurrence, for a total treatment period of 3 days. The same treatment was given for the patient's second migraine episode, and the patient was monitored until the first to occur of (i) a third episode or (ii) expiry of 2 months from the start of the run-in period.

During the therapeutic period of the study, the patients treated themselves as during the run-in period with either placebo, 0.5 mg patches, or 1.0 mg patches as described above.

Throughout the duration of the study the patients recorded in a patient diary the dates, times, severity, and treatments of their migraine attacks. No treatment with other migraine prophylactic agents was allowed during the study, nor was treatment with sumatriptan allowed. Other acute treatments were allowed during the study.

A statistical analysis of the results from the first 115 patients enrolled in the study was conducted. Of these patients 2 were lost to follow-up and 27 failed to report properly recorded results or were not analyzable for all criteria. Of the remaining 88 patients 27 were placebo treated, 29 were 0.5 mg treated, and 32 were 1.0 mg treated. Results are summarized in the TABLES that follow. Proportion of males and females in each treatment were compared using a chi-square test. All other results in each treatment were compared using analysis of variance methods. If the overall test for treatment differences was statistically significant ($p<0.05$), pairwise comparisons among the treatment groups were further tested using a Student-Newman-Keuls multiple range test. Results shown in bold italics were found to be different from results obtained for the other treatment groups at the 5% level of statistical significance. P-values presented in the tables correspond to the significance level for the overall test of treatment differences.

|  | AGE (Years) | | |
|---|---|---|---|
|  | Placebo | 0.5 mg | 1.0 mg |
| MEAN | 41.11 | 37.72 | 39.00 |
| Standard Deviation | 8.46 | 10.19 | 6.92 |
| Minimum | 25 | 18 | 27 |
| Maximum | 57 | 60 | 52 |
| n | 27 | 29 | 32 |
| Analysis of Variance |  | $P = 0.33$ |  |

|  | GENDER | | | | | |
|---|---|---|---|---|---|---|
|  | Placebo | | 0.5 mg | | 1.0 mg | |
|  | M | F | M | F | M | F |
| n | 6 | 21 | 8 | 21 | 14 | 18 |
| % | 22.2 | 77.8 | 27.6 | 72.4 | 43.8 | 56.3 |
| All | 27 | | 29 | | 32 | |
| Chi-square Test |  |  | $P = 0.18$ |  |  |  |

CONTRAST ANALYSIS

In the Tables that follow, $T_{basal}$ = mean time between episodes during run-in
$T_1$ = time to first recurrence under treatment
$T_2$ = time from first to second recurrence under treatment $R_1 = T_1/T_{basal}$
$R_2 = T_2/T_{basal}$
$R_{tot} = (T_1+T_2)/2(T_{basal})$

|  | Placebo (days ± sd) | 0.5 mg (days ± sd) | 1.0 mg (days ± sd) | P Values |
|---|---|---|---|---|
| $T_{basal}$ | 8.34 ± 2.71 | 7.41 ± 2.95 | 7.60 ± 2.78 | 0.43 |
| $T_1$ | 11.04 ± 7.15 | 10.24 ± 5.27 | 10.59 ± 7.67 | 0.91 |
| $T_2$ | 8.04 ± 5.19 | 11.72 ± 6.46 | 7.81 ± 5.84 | 0.02 |

|  | Placebo | 0.5 mg | 1.0 mg | P Values |
|---|---|---|---|---|
| $R_1$ | 1.45 ± 1.03 | 1.54 ± 0.83 | 1.43 ± 0.81 | 0.87 |
| $R_2$ | 0.94 ± 0.49 | 1.78 ± 1.10 | 1.11 ± 0.84 | 0.0007 |
| $R_{tot}$ | 1.19 ± 0.53 | 1.66 ± 0.74 | 1.27 ± 0.67 | 0.02 |
| $T_1 - T_{basal}$ | 2.70 ± 7.32 | 2.83 ± 5.61 | 2.99 ± 7.16 | 0.99 |
| $T_2 - T_{basal}$ | −0.30 ± 4.12 | 4.31 ± 6.77 | 0.21 ± 6.06 | 0.005 |

|  | MALES | | | |
|---|---|---|---|---|
| MEAN VALUES | PLACEBO (n = 6) (days ± sd) | 0.5 mg (n = 8) (days ± sd) | 1.0 mg (n = 14) (days ± sd) | P Value |
| $T_{basal}$ | 7.54 ± 2.03 | 7.44 ± 3.08 | 6.93 ± 1.62 | 0.80 |
| $T_1$ | 11.00 ± 5.59 | 10.00 ± 4.93 | 11.93 ± 8.13 | 0.82 |
| $T_2$ | 7.67 ± 4.93 | 8.88 ± 5.00 | 8.29 ± 6.63 | 0.93 |
| $R_1$ | 1.76 ± 1.50 | 1.53 ± 0.76 | 1.70 ± 0.88 | 0.90 |
| $R_2$ | 1.02 ± 0.57 | 1.29 ± 0.71 | 1.24 ± 1.11 | 0.85 |
| $R_{tot}$ | 1.39 ± 0.79 | 1.41 ± 0.50 | 1.47 ± 0.84 | 0.97 |

|  | FEMALES | | | |
|---|---|---|---|---|
| MEAN VALUES | PLACEBO (n = 21) (days ± sd) | 0.5 mg (n = 21) (days ± sd) | 1.0 mg (n = 18) (days ± sd) | P Value |
| $T_{basal}$ | 8.57 ± 2.87 | 7.40 ± 2.98 | 8.12 ± 3.38 | 0.47 |
| $T_1$ | 11.05 ± 7.66 | 10.33 ± 5.51 | 9.56 ± 7.37 | 0.80 |
| $T_2$ | 8.14 ± 5.38 | 12.81 ± 6.72 | 7.44 ± 5.32 | 0.009 |
| $R_1$ | 1.36 ± 0.88 | 1.55 ± 0.87 | 1.22 ± 0.71 | 0.47 |
| $R_2$ | 0.92 ± 0.48 | 1.97 ± 1.18 | 1.01 ± 0.56 | 0.0001 |
| $R_{tot}$ | 1.40 ± 0.43 | 1.76 ± 0.80 | 1.12 ± 0.48 | 0.001 |

The results in the TABLES above show a statistically significant improvement in the 0.5 mg treatment group when compared to the placebo and 1.0 mg treatment groups. This difference was only observed in females. No significant differences were observed in $T_1$ among the three treatment groups.

The claimed invention is:

1. A method of reducing the frequency of and/or preventing migraine, comprising the step of administering melatonin in an amount and for a time sufficient to increase the period of time between episodes of migraine, wherein the melatonin is administered to and across a mucosal surface.

2. A method according to claim 1, wherein the mucosal surface is an oral mucosal surface.

3. A method according to claim 1, wherein the melatonin is delivered from a device comprising a mucoadhesive matrix having melatonin dissolved or substantially uniformly dispersed therein.

4. A method according to claim 3, wherein the device comprises a mucoadhesive matrix comprising:

1) a particulate polymeric resin with an average particle size of less than or equal to about 100 µm, and comprising at least about 55% by weight of carboxylic acid moieties based on the total weight of the polymeric resin;

2) from about 20 parts to about 250 parts by weight of a hydrophobic elastomeric component, based on 100 parts by weight of the resin; and 3) from about 0.1 to about 20 parts by weight of melatonin based on 100 parts by weight of the resin;

wherein the resin is dispersed substantially throughout the elastomeric component, and which composition contains less than about 10 by weight of water based on the total weight of the resin.

5. A method according to claim 1, wherein the melatonin is delivered according to an administration cycle comprising delivering melatonin in an amount of about 0.05 to about 5 milligrams over a period of about 10–12 hours commencing between about 1 to about 5 hours before the normal onset of sleep on the day of a migraine attack.

6. A method according to claim 5, comprising the further step of repeating the administration cycle on the first day following the migraine attack.

7. A method according to claim 6, comprising the further step of repeating the administration cycle on the second day following the migraine attack.

* * * * *